United States Patent [19]

Isobe

[11] Patent Number: 5,034,617
[45] Date of Patent: Jul. 23, 1991

[54] METHOD AND APPARATUS FOR MEASURING REFRACTIVE INDEX AND THICKNESS OF FILM

[75] Inventor: Tami Isobe, Yokohama, Japan
[73] Assignee: Ricoh Company, Ltd., Tokyo, Japan
[21] Appl. No.: 330,087
[22] PCT Filed: Sep. 16, 1988
[86] PCT No.: PCT/JP88/00941
  § 371 Date: Mar. 17, 1989
  § 102(e) Date: Mar. 17, 1989
[87] PCT Pub. No.: WO89/02572
  PCT Pub. Date: Mar. 23, 1989

[30] Foreign Application Priority Data

Sep. 18, 1987 [JP] Japan ................... 62-234119

[51] Int. Cl.$^5$ ........................... G01N 21/86
[52] U.S. Cl. ........................ 250/560; 356/357
[58] Field of Search ............... 250/560; 356/328, 355, 356/357, 358, 361, 317, 318, 382

[56] References Cited

U.S. PATENT DOCUMENTS

| | | | |
|---|---|---|---|
| 3,601,492 | 8/1971 | Reichard | 356/357 |
| 4,498,772 | 2/1985 | Jastrzebski et al. | 356/361 |
| 4,625,114 | 11/1986 | Bosacchi et al. | 356/318 |
| 4,707,611 | 11/1987 | Southwell | 250/560 |

FOREIGN PATENT DOCUMENTS

| | | |
|---|---|---|
| 4838169 | of 0000 | Japan . |
| 533363 | 1/1978 | Japan . |
| 62-11106 | 1/1987 | Japan . |
| 62-119403 | 5/1987 | Japan . |
| 62-134507 | 6/1987 | Japan . |
| 0737817 | 5/1980 | U.S.S.R. ............... 356/361 |

OTHER PUBLICATIONS

Raif et al., "Rapid Nondestructive Method for Measuring the Refractive Index and Thickness of Thin Dielectric Films" Aug. 1972, pp. 48–50.
Warnecke et al., IBM J. Res. Develop, pp. 256–262 "Refractive Index Dispersion in Semiconductor-Related Thin Films".

Primary Examiner—David C. Nelms
Attorney, Agent, or Firm—Oblon, Spivak, McClelland, Maier & Neustadt

[57] ABSTRACT

A method for measuring a refractive index and a thickness of a dielectric thin film formed on a substrate. The method comprises the following four steps. A step for irradiating a thin film on a substrate with a monochromatic light of a wavelength $\lambda$, changing the incident angle thereof so as to measure a change of the energy reflection ratio or reflectance in response to changes of the incident angle and detect two incident angles $\theta 1$ and $\theta 2$ which correspond to two extreme values of the reflectance change. A step for irradiating the thin film with a monochromatic light of a wavelength $\lambda'$, changing an incident angle thereof so as to measure change of reflectance in response to the change of the incident angle and detect an incident angle $\theta 3$ which corresponds to an extreme value of the energy change. A step for calculating the refractive indices and thicknesses of the thin film, on the basis of the incident angle values $\theta 1$ and $\theta 2$, changing the interference degree number used as a parameter. And a step for determining the thickness of the thin film and the refractive indices thereof with respect to the light of a wavelength $\lambda$ and the light of a wavelength $\lambda'$, on the basis of the incident angle value $\theta 3$ and the data calculated as mentioned above. The method makes it possible to easily and accurately carry out the measurement.

8 Claims, 2 Drawing Sheets

METHOD AND APPARATUS FOR MEASURING REFRACTIVE INDEX AND THICKNESS OF FILM

DESCRIPTION

1. Field of the Invention

The present invention relates to a method and an apparatus for measuring the refractive index and thickness of a dielectric thin film formed on a substrate.

2. Background Art

In connection with the semiconductor related techniques or the like, it has become very important to develop an art for non-destructively measuring the refractive index and thickness of a dielectric thin film formed on a substrate.

In the state of art, a method called "LASER VAMFO" (LASER USING VARIABLE ANGLE MONOCHROMATIC FRINGE OBSERVATION) is known as method for measuring the refractive index and thickness of a thin film aiming to heighten the accuracy of the measurement (see REFRACTIVE INDEX DISPERSION IN SEMICONDUCTOR RELATED THIN FILMS: IBM J. RES. DEVELOP. MAY 1973). However, this known method has problems in that a large scale apparatus is necessitated for carrying out the method since a monochrometer must be used for the measurement and that it takes a relatively long time for the measurement.

SUMMARY OF THE INVENTION

The present invention was made considering the above mentioned problems of the state of the art. Therefore, it is an object of the present invention to provide a novel method and apparatus for measuring the refractive index and thickness of a dielectric thin film formed on a substrate wherein it becomes possible to carry out the measurement easily and accurately.

In accordance with the present invention, there is provided a method for measuring the refractive index of a dielectric thin film formed on a substrate, the method comprising the following four steps from a first step to a fourth step.

The first step is to irradiate a thin film on a substrate with a monochromatic light having a wavelength $\lambda$, changing an incident angle thereof so as to measure change of energy reflection ratio in response to the change of the incident angle and detect two incident angles $\theta 1$ and $\theta 2$ which correspond to an arbitrary two of the extreme values of the energy reflection ratio change, respectively. The second step is to irradiate the thin film on the sutstrate with a monochromatic light having a wavelength $\lambda'$, changing an incident angle thereof so as to measure change of energy reflection ratio, i.e., reflectance in response to the change of the incident angle and detect one incident angle $\theta 3$ which corresponds to on arbitrary one of the extreme value of the energy change. The third step is to calculate the refractive indices and thicknesses of the thin film, on the basis of the incident angle values $-\theta 1$ and $\theta 2$, with respect to a series of the interference degree numbers being used as parameters of the calculation. The fourth step is to determine the thickness of the thin film and the refractive index thereof with respect to the light having a wavelength $\lambda$ and the light having a wavelength $\lambda'$, respectively, on the basis of the incident angle value $\theta 3$ and the values of the refractive indices and thicknesses calculated in the third step. The sequence of the steps may be in the order of the above mentioned steps from the first step to the fourth step. Or otherwise, the order of the second step and the third step may be exchanged for each other.

DESCRIPTION OF THE PREFERRED EMBODIMENTS

Figure 3:
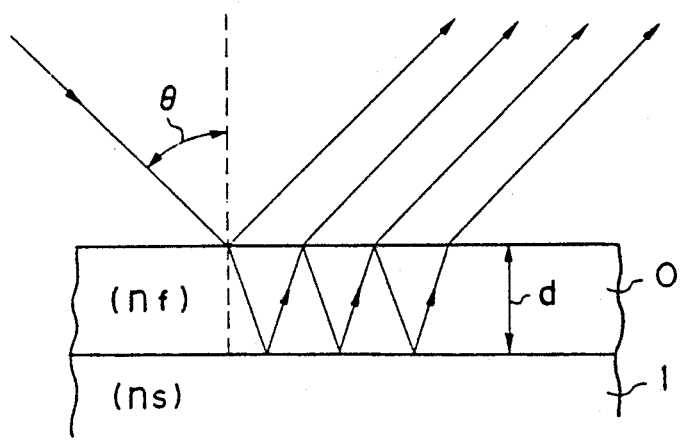
FIG. 3 is an explanatory view for explaining the present invention.

The principle of the present invention will now be explained hereinafter with respect to an actual example of the invention. FIG. 3 represents a dielectric thin film 0 coated on a substrate 1 having a refractive index $n_s$ in a state in which a light irradiates the thin film at an incident angle $\theta$ and the light is reflected by the thin film.

Objects which are to be measured are refractive index $n_f$ and thickness d of the thin film 0.

When the incident angle $\theta$ changes, the energy reflection ratio or reflectance also changes accordingly. The curve of the change of the energy reflection ratio has a convex peak and a concave bottom due to an interference phenomenon.

On the condition that the refractive index $n_s$ is larger than the refractive index $n_f$ ($n_s > n_f$), the energy reflection ratio is maximized at an incident angle $\theta$ which satisfies the following equation.

$$2d\sqrt{n_f^2 - \text{SIN}^2\theta} = m\lambda \qquad (1)$$

Whereas the energy reflection ratio or reflectance is minimized at an incident angle $\theta$ which satisfies the following equation.

$$2d\sqrt{n_f^2 - \text{SIN}^2\theta} = \{m + (\tfrac{1}{2})\}\lambda \qquad (2)$$

On the other hand, on the condition that the refractive index $n_s$ is smaller than the refractive index $n_f$ ($n_s < n_f$), the energy reflection ratio or reflectance is minimized when the equation (1) is satisfied, whereas the energy reflection ratio or reflectance is maximized when the equation (2) is satisfied.

When the refractive index $n_s$ is larger than the refractive index $n_f$ ($n_s > n_f$) and when two minimum extreme values of the energy reflection ratio are obtained at incident angles $\theta 1$ and $\theta 2$, respectively, the following equations are derived from the equation (2) wherein the interference degree number $m_1$ and $m_2$ are represented by a whole number plus a half of one.

$$2d\sqrt{n_f^2 - \text{SIN}^2\theta 1} = m_1\lambda \qquad (3\text{-}1)$$

$$2d\sqrt{n_f^2 - \text{SIN}^2\theta 2} = m_2\lambda \qquad (3\text{-}2)$$

By eliminating the value d of the film thickness from the above two equations, the following equation with regard to the refraction index $n_f$ is obtained.

$$n_f = \{(m_1^2 \cdot \text{SIN}^2\theta_2 - m_2^2 \cdot \text{SIN}^2\theta_1)/(m_1^2 - m_2^2)\}^{\frac{1}{2}} \quad (4)$$

An actual example is described below.

The substrate 1 of FIG. 3 is made from Si and the thin film 0 is made from $SiO_z$. A laser beam of He—Ne having a wavelength 6328 Å is irradiated onto the thin film, changing the angle of incidence. The energy reflection ratio is detected or reflectance in relation to the angle of incidence. The two incident angle values $\theta_1$ and $\theta_2$ which minimize the energy reflection ratio are 36.4 degrees for $\theta_1$ and 60.2 degrees for $\theta_2$, respectively. In this case, relation between the interference degree numbers $m_1$ and $m_2$ can be represented as $m_1 = m_2 + 1$, since the minimum extreme values at the incident angles $\theta_1$ and $\theta_2$ are adjacent to each other representing at the angle 36.4 degrees first and at the angle 60.2 degrees subsequently.

The equation (4) mentioned above is calculated by substituting the above mentioned values for $\theta_1$ and $\theta_2$ in the equation (4). The calculation result is substituted for the corresponding factor in the above mentioned equations (3-1) and (3-2) to calculated the equations so that the refractive index $n_f$ and the film thickness d can be obtained for each number of a series of the interference degree number $m_1$ which is used as a parameter of the calculation. A part of the calculation result is represented in a table 1 below.

TABLE 1

| $m_1$ | $n_f$ | d (Å) |
|---|---|---|
| 5.5 | 1.25091 | 15802.8 |
| 6.5 | 1.32799 | 17311.1 |
| 7.5 | 1.401 | 18698.1 |
| 8.5 | 1.47049 | 19989.1 |
| 9.5 | 1.5369 | 21201.7 |
| 10.5 | 1.60061 | 22348.5 |

With regard to the thin film of $SiO_z$, a genuine value of the refractive index is 1.470 and a genuine value of the film thickness is 20000 Å. Therefore, a genuine value of the interference degree number for the incident angle $\theta_1$ is 8.5. However, the genuine value 8.5 can not be selected from the table in accordance with the process so far mentioned above. Accordingly, it is not able to determine the genuine values of the refractive index and the thickness of the thin film from the table.

Referring again to the measuring process so far mentioned above, the step in which the incident angles $\theta_1$ and $\theta_2$ are detected is the first step referred to in the beginning portion of this disclosure of the invention. Also, the third step mentioned there is the step in which the refractive index and the thickness of the thin film are calculated for each of the interference degree numbers used as parameters of the calculation on the basis of the incident angles $\theta_1$ and $\theta_2$ detected in the first step.

After that, a laser beam of He—Ne having a wavelength 5941 Å which is different from the wavelength 6328 Å used in the first step mentioned above is irradiated to the thin film so as to detect an incident angle $\theta_3$ which minimizes the energy reflection ratio or reflectance with respect to the He—Ne laser beam having the wavelength 5941 Å. The detection result of the incident angle $\theta_3$ was 24.5 degrees. The above mentioned two wavelengths are close to each other and the incident angle $\theta_3$ is close to the angle $\theta_1$. Therefore, the interference degree number of the laser beam irradiated with the incident angle $\theta_3$ is supposed to be the same as the interference degree number $m_1$ of the laser beam irradiated with the incident angle $\theta_1$ or slightly larger than $m_1$ by 1 or 2.

By solving the equation (1) with respect to the refractive index $n_f$, the following equation $$n_f = \{(m^2 \cdot \lambda^2 / 4d^2) + \text{SIN}^2\theta\}^{\frac{1}{2}} \quad (5)$$

can be obtained. In this equation, the film thickness d is constant with respect to the wavelength. Therefore, the following calculation can be carried out. The incident angle $\theta_3 = 24.5$ is substituted for the $\theta$ represented in the right side of the equation. Also, with respect to the film thickness d, each of the series of values of the film thickness calculated in the third step mentioned above is substituted for the film thickness d represented in the right side of the equation. Each of the film thickness values calculated in the third step is derived by changing the interference degree number $m_1$ as the parameter of the calculation. With respect to the interference degree number m in the equation, m is assumed to be $m_1$, $m_1 + 1$, and $m_1 + 2$, respectively, so that the refractive index of the thin film is calculated from the equation (5) with regard to each of the interference degree numbers $m_1$, $m_1 + 1$, and $m_1 + 2$ in which $m_1$ is changed as the parameter of the calculation. A part of the calculation result is represented in tables 2 to 4. In the table 2, $m_1$ is substituted for the interference degree number m represented in the right side of the equation (5). Also, in tables 3 and 4, $m_1 + 1$ and $m_1 + 2$ are substituted for the interference degree number m represented in the equation, respectively.

TABLE 2

| $m_1$ | $n_f$ | d | m | $n_f'$ |
|---|---|---|---|---|
| 5.5 | 1.25091 | 15802.8 | 5.5 | 1.11392 |
| 6.5 | 1.32799 | 17311.1 | 6.5 | 1.18997 |
| 7.5 | 1.401 | 18698.1 | 7.5 | 1.2616 |
| 8.5 | 1.47049 | 19989.1 | 8.5 | 1.32948 |
| 9.5 | 1.5369 | 21201.7 | 9.5 | 1.39412 |
| 10.5 | 1.60061 | 22348.5 | 10.5 | 1.45594 |

TABLE 3

| $m_1$ | $n_f$ | d | m | $n_f'$ |
|---|---|---|---|---|
| 5.5 | 1.25091 | 15802.8 | 6.5 | 1.29028 |
| 6.5 | 1.32799 | 17311.1 | 7.5 | 1.35213 |
| 7.5 | 1.401 | 18698.1 | 8.5 | 1.4126 |
| 8.5 | 1.47049 | 19989.1 | 9.5 | 1.4714 |
| 9.5 | 1.5369 | 21201.7 | 10.5 | 1.52845 |
| 10.5 | 1.60061 | 22348.5 | 11.5 | 1.5838 |

TABLE 4

| $m_1$ | $n_f$ | d | m | $n_f'$ |
|---|---|---|---|---|
| 5.5 | 1.25091 | 15802.8 | 7.5 | 1.46952 |
| 6.5 | 1.32799 | 17311.1 | 8.5 | 1.51637 |
| 7.5 | 1.401 | 18698.1 | 9.5 | 1.56517 |
| 8.5 | 1.47049 | 19989.1 | 10.5 | 1.61453 |
| 9.5 | 1.5369 | 21201.7 | 11.5 | 1.66374 |
| 10.5 | 1.60061 | 22348.5 | 12.5 | 1.71243 |

In the above tables 2 and 3, the refractive index $n_f$ represents the calculation result with regard to the wavelength 6328 Å which is used for the calculation in the third step, whereas the refractive index $n_f'$ listed in the right end column of the tables represents the calculation result with regard to the wavelength 5941 Å which is used for the calculation in accordance with the equation (5). Reviewing the refractive indices $n_f$ and $n_f'$ in comparison to each other in the tables 2 to 4, it can be seen that, in the table 2, $n_f$ is always larger than $n_f'$ ($n_f > n_f'$) regardless of the value of the parameter $m_1$. Whereas, in the table 4, $n_f$ is always smaller than $n_f'$ ($n_f < n_f'$) regardless of the value of the parameter $m_1$. Also, the difference between the refractive indices $n_f$ and $n_f'$ is larger than the refractive index change due to dispersion. Therefore, it is not adequate to adopt $m_1$ or $m_1 + 2$ as the interference degree number m. On the other hand, in the table 3, with respect to the refractive indices $n_f$ and $n_f'$, the larger refractive index is changed between the two according to the value of the parameter $m_1$. The difference between the two refractive indices is minimized when $m_1 = 8.5$ wherein the difference $n_f' - n_f = 0.00091$. Consequently, from the fact mentioned above, it is able to specify the thickness of the thin film to be 19989.1 Å. Also, the refractive indices for the wavelengths 6328 Å and 5941 Å can be specified as 1.47049 and 1.4714, respectively. The refractive index for wavelength 5941 Å is slightly larger than the refractive index for wavelength 6328 Å, which is in accord with Sellmeier's Law of Dispersion according to which the refractive index of a dielectric material with regard to light in a visible range is slightly decreased as the wavelength of the light increases.

The fourth step mentioned before comprises the above mentioned process in which the refractive index and the thickness of the thin film are specified on the basis of the incident angle $\theta 3$ obtained in the second step and the data obtained in the third step.

As can be seen from the above description, the fourth step includes the calculation to obtain the refractive index $n_f'$ in accordance with the equation (5) on the basis of the data calculated in the third step, i.e., the data of film thickness with respect to the interference degree number $m_1$ used as a parameter of the calculation and the incident angle $\theta 3$ detected in the second step and it also includes the calculation to specify the film thickness and the refractive index for each of different wavelengths by comparing the refractive index $n_f'$, calculated as mentioned above, with the refractive index $n_f$, calculated in the third step, so as to choose a parameter $m_1$ which makes the two refractive indices closest to each other and makes the refractive index with respect to the shorter wavelength longer than with respect to the longer wavelength.

In the calculation to obtain the refractive index $n_f'$, the calculation is carried out in such a way that the interference degree number m in the equation (5) is increased one by one from the parameter $m_1$ or decreased one by one from the parameter $m_1$ so that the calculation is repeated until the larger refractive index is changed between the two refractive indices $n_f$ and $n_f'$ in response to the change of the parameter $m_1$. If the wavelengths of the two lights are too far different from each other, the difference between the degree numbers of the extreme values which correspond to the wavelength of the light may become large as well as the dispersion of the refractive index with respect to the wavelength. Therefore, it is desirable to select the two wavelengths of the light which differ not so much from each other to minimize the difference therebetween.

The present invention is further described below referring to an embodiment in actual use.

Figure 1:
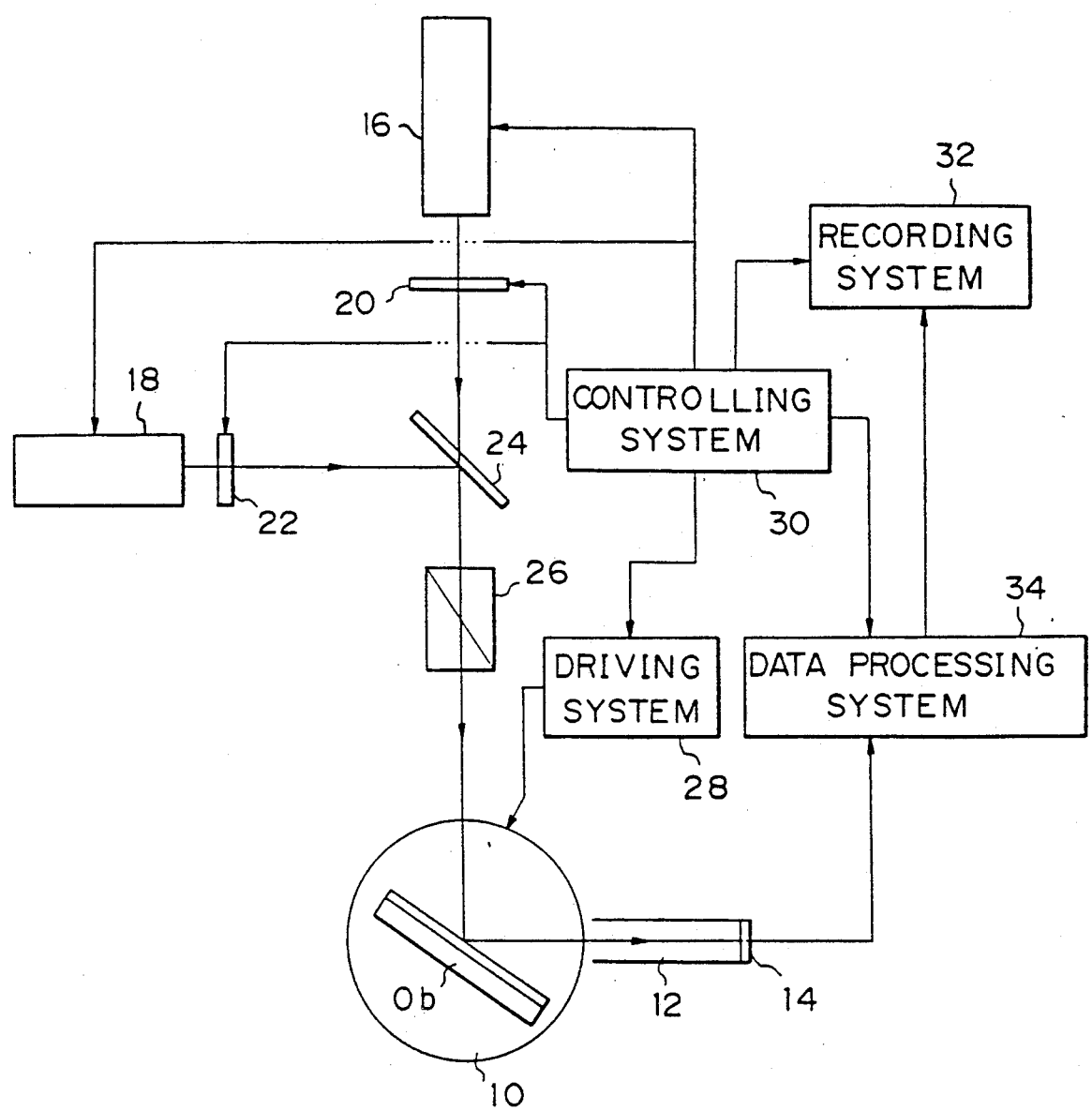
FIG. 1 is an explanatory view for explaining an embodiment of the present invention.

A sample Ob to be measured comprises a substrate of Si on which a thin film of $SiO_2$ is coated by a sputtering method. The measuring sample Ob is placed on a turn table 10 as illustrated in FIG. 1. An arm 12 is arranged coaxial with the turn table 10. The arm 12 is arranged in such a way that when the turn table 10 is rotated by a driving system 28, the arm 12 is rotated at a rotational speed twice that of the turn table 10 so that the rotational angle of the arm 12 is twice as that of the turn table 10. A sensor 14 for detecting the light reflected from the sample Ob is mounted on the arm 12 at an end thereof.

Numeral 16 designates a laser source of He—Ne having a wavelength of 6328 Å and numeral 18 designates a laser source of He—Ne having a wavelength of 5941 Å. Numerals 20 and 22 designate shutters. Numeral 24 designates a dichroic mirror. The dichroic mirror 24 is designed in such a way that the transmission factor thereof with regard to the laser beam of wavelength 6328 Å is large whereas the reflection ratio thereof with regard to the laser beam of wavelength 5941 Å is large. Therefore, it becomes possible to change the wavelength of the incident light irradiated to the measuring sample Ob by driving the shutters 20 and 22.

The incident light is adjusted to become an S-polarized light with respect to the incident plane by a Glan-Thomson prism 26. The reason for using the S-polarized light as the incident light is that if a P-polarized light is used, the difference between the maximum extreme value and the minimum extreme value of the energy reflection ratio becomes unclear due to the Brewster's angle.

The incident angle is set to be zero at the starting point of the measurement and increased in the measuring process by rotating the turn table 10 and the arm 12. In this case, the sensor 14 always receives the reflection light from the sample without fail since the rotation angle of the arm 12 is arranged to be twice as that of the turn table 10.

The turn table 10 and the arm 12 are driven to be rotated by the driving system 28 which is controlled by a controlling system 30. The controlling system 30 also controls the laser sources 16 and 18, the shutters 20 and 22, a data processing system 34 and recording system 32. The data processing system 34 carries out the calculation of the third step and the fourth step as mentioned above. The recording system 32 records the result of the above mentioned calculation. The controlling system 30 and the data processing system 34 can be realized by a computer system. Also, the recording system 32 may comprises a display means such as a CRT (cathode ray tube) or a printer means.

First in operation, the shutter 22 is closed and the other shutter 20 is opened so that the laser beam of wavelength 6328 Å is adjusted to be the S-polarized light and irradiated onto the sample Ob placed on the turn table 10 which is rotated to change the incident angle of the light with respect to the sample. The energy reflection ratio or reflectance of the light reflected from the sample changes in response to the change of the incident angle. The change of the energy of reflection is detected by the sensor 14 as the output change thereof so that two incident angles with which the energy reflection ratio or reflectance becomes a maximum extreme value are detected. The two incident angles $\theta 1$ and $\theta 2$ are detected as 28.5 degrees and 48.8 degrees at which angles the energy reflection ratio curve represents two peak extreme values which are adjacent to each other (the first step). Therefore, the interference degree numbers of the two incident angles are different from each other by a degree number of 1.

After that, the shutter 20 is closed and the shutter 22 is opened instead so that the incident light is changed to the laser beam of wavelength 5941 Å. With the use of this laser beam, one incident angle $\theta_3$ with which angle the energy reflection ratio or reflectance becomes a maximum extreme value is detected. The detected incident angle $\theta_3$ is 42.7 degrees (the second step). With regard to this measuring sample, the refractive index of the thin film is supposed to be lower than that of the substrate. Therefore, the interference degree numbers $m_1$ and $m_2$ represented in the right sides of the equations (3-1) and (3-2) are natural numbers.

In accordance with the equations (3-1), (3-2) and (5), the refractive index $n_f$ and the film thickness d are calculated using the interference degree number $m_1$ as a parameter of the calculation (the third step).

After that, the data calculated as mentioned above and the incident angle 42.7 degrees are substituted for the factors in the equation (5) so that the refractive index $n_f'$ for the wavelength 5941 Å is calculated using $m_1+1$ as the interference degree number m. Also, a parameter $m_1$ is selected which parameter makes a state in which the difference between the refractive indices $n_f$ and $n_f'$ becomes smallest and in which $n_f$ is smaller than $n_f'$ ($n_f < n_f'$).

The refractive index and the film thickness corresponding to this parameter are specified as a genuine value of measurement result (the fourth step). A part of the calculation result is represented in table 5. Actually, the calculation was repeated changing the parameter $m_1$ from 2 to 20.

TABLE 5

| $m_1$ | $n_f$ | d | m | $n_f'$ |
|---|---|---|---|---|
| 8 | 1.29295 | 21063.7 | 9 | 1.31633 |
| 9 | 1.35657 | 22424.1 | 10 | 1.3716 |
| 10 | 1.41739 | 23706.5 | 11 | 1.42478 |
| 11 | 1.47573 | 24923 | 12 | 1.47607 |
| 12 | 1.53188 | 26082.8 | 13 | 1.52566 |
| 13 | 1.58606 | 27193.2 | 14 | 1.5737 |

As can be seen from the table 5, the refractive index which is specified as the genuine value of the measurement is the one which minimizes the difference between $n_f$ and $n_f'$, i.e., the one which is selected when the parameter $m_1$ is 11 in which the $n_f$ and $n_f'$ are 1.47573(6328 Å) and 1.47607(5941 Å), respectively. Also, the film thickness is 24923 Å.

As mentioned above with reference to an embodiment of the present invention, it is possible to obtain a genuine value of the refractive index and the film thickness by a calculation on the basis of incident angles which make a state in which a peak extreme value of the energy reflection ratio or reflectance is represented.

Figure 2:
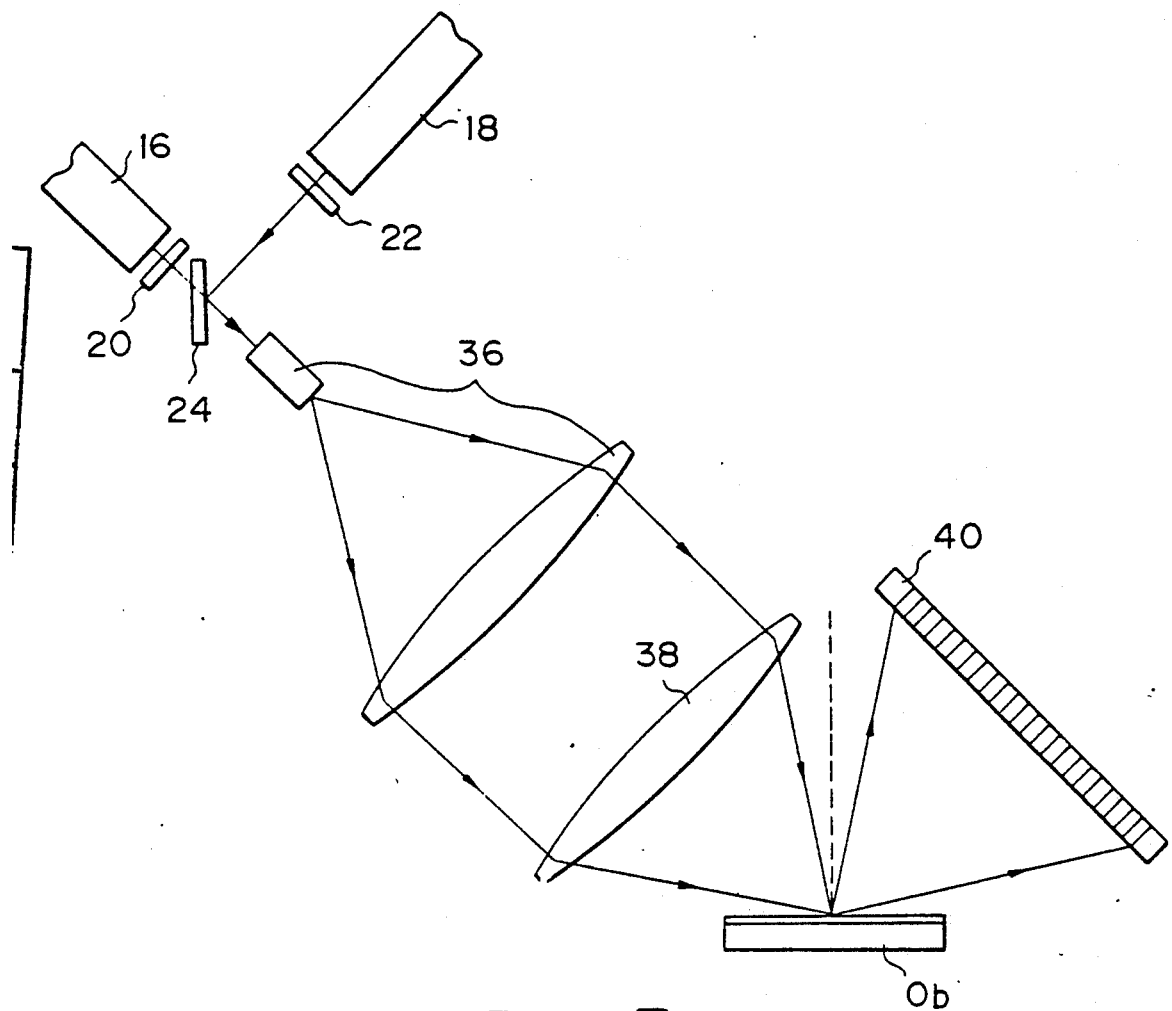
FIG. 2 is an explanatory view for explaining another embodiment of the present invention.

Another embodiment of the present invention is illustrated in FIG. 2.

A measurement sample Ob comprises a glass substrate of Pyrex (trade name) on which a nitride film is coated by a plasma CVD method. Objects of the measurement are the refractive index and the thickness of the nitride film.

The incident light irradiated onto the sample is arranged in such a way that the diameter of the laser beam from the light source is expanded by a beam expander 36, then the beam is converged by a condenser lens 38 to irradiate the sample Ob which is unmovably supported. With this arrangement, it becomes possible to irradiate the sample by a light from continuously different angles of incidence at a time.

Also, the reflection light reflected from the sample is collectively received by a photosensor array 40 at a time. The output of the photosensor array 40 is read in a time sequence by a data processing system by driving a controlling system similar to the one shown in FIG. 1 so that the incident angles which give an extreme value are detected so as to carry out the calculation on the basis of the detected data. The data processing system and the recording system are similar to those of the embodiment of FIG. 1.

In the state that the shutter 20 is opened to irradiate the sample with the incident light of wavelength 6328 Å, the incident angles $\theta_1$ and $\theta_2$ which make the energy reflection ratio or reflectance minimized are detected (the first step). The detection data were 31.4 degrees and 56.5 degrees. Also, in the state that the shutter 22 is opened to irradiate the sample with the incident light of wavelength 5941 Å, the incident angle $\theta_3$ which makes the energy reflection ratio minimized is detected (the second step). The detection data was 56.8 degrees.

In this case, the refractive index $n_s$ of the substrate is smaller than the refractive index $n_f$ of the thin film. Therefore, the interference degree numbers $m_1$ and $m_2$ of the right sides of the equations (3-1) and (3-2) are a natural number. The third step and the fourth step are carried out in a same manner as in the embodiment mentioned before. A part of the calculation result is represented in table 6. Actually, the calculation was carried out changing the parameter $m_1$ from 2 to 20.

TABLE 6

| $m_1$ | $n_f$ | d | m | $n_f'$ |
|---|---|---|---|---|
| 12 | 1.71042 | 23305.6 | 13 | 1.74205 |
| 13 | 1.77119 | 24297.8 | 14 | 1.79478 |
| 14 | 1.82996 | 25251 | 15 | 1.84602 |
| 15 | 1.88692 | 26169.5 | 16 | 1.87588 |
| 16 | 1.94221 | 27056.9 | 17 | 1.94448 |
| 17 | 1.99598 | 27916 | 18 | 1.99189 |

As can be seen from table 6, the refractive indices specified as the genuine values of the measurement are 1.94221(6328 Å) and 1.94448(5941 Å) when the parameter $m_1$ is 16. Also, the film thickness is specified to be 27056.9 Å as the genuine value of the measurement.

As mentioned above, in accordance with the present invention, a novel method for measuring the refractive index and thickness of a thin film can be provided. The method of the present invention comprising the above mentioned arrangement makes it possible to easily and accurately measure the refractive index and the thickness of a dielectric thin film.

Note that the above mentioned explanation refers to the embodiments in which an absorption coefficient of the substrate is zero or negligible. When the absorption coefficient of the substrate is large, for instance when a substrate of aluminum is used, it is necessary to correct the calculated value of the film thickness d obtained in the third step and the fourth step mentioned above. Such correction can be made in accordance with a known method of "PHASE-SHIFT THICKNESS CORRECTION" which is disclosed in a document "PHASE-SHIFT CORRECTION IN DETERMINING THE THICKNESSES OF TRANSPARENT FILMS ON REFLECTIVE SUBSTRATES (SOLID STATE ELECTRONICS PERGAMON PRESS 1968 VOL. 11, PP957-963). Subsequent calculation process after the correction is made is the same as the process of the above mentioned embodiments.

INDUSTRIAL APPLICABILITY

The present invention can be applied to a device for forming thin films such as dielectric films, wiring pattern films and semiconductor films in a process for manufacturing semiconductor related devices. For example, the present invention can be applied to a vacuum evaporation device, a sputtering device, a PVD device, a CVD device and an epitaxial diffusing device.

I claim:

1. An apparatus for measuring a refractive index and a thickness of a thin film formed on a substrate, comprising:

a first light source for emitting a first monochromatic light having a wavelength $\lambda$;

a second light source for emitting a second monochromatic light having a wavelength $\lambda'$, which is different from that of said first monochromatic light;

a light changing means for changing a light to be irradiated onto said thin film by selecting one of said emitted first monochromatic light and said emitted second monochromatic light;

an incident angle changing means for changing an incident angle of said selected monochromatic light and for detecting said changed incident angle of said selected monochromatic light;

a detection means adapted to detect a reflection light reflected from said substrate, to measure a reflectance of said detected reflection light, to determine two arbitrary minima or two arbitrary maxima of said measured reflectance corresponding to a change of said incident angle of said first monochromatic light on the basis of said detected incident angle of said emitted first monochromatic light to thereby determine respectively two incident angles $\theta_1$ and $\theta_2$ corresponding to said determined two arbitrary minima or said determined two arbitrary maxima when said emitted first monochromatic light is selected by said light changing means, and to determine a single minimum or maximum of said measured reflectance corresponding to a change of said incident angle of said second monochromatic light on the basis of said detected incident angle of said emitted second monochromatic light to thereby determine an incident angle $\theta_3$ corresponding to said single minimum or maximum when said emitted second monochromatic light is selected by said light changing means; and a calculation means adapted to calculate refractive indices and thicknesses of said thin film on the basis of said wavelength $\lambda$ and said determined two incident angles $\theta_1$ and $\theta_2$ as varying orders of interference $m_1$ and $m_2$ as parameters according to the following equations:

$$2d\sqrt{n_f^2 - \sin^2\theta_1} = m_1\lambda$$

$$2d\sqrt{n_f^2 - \sin^2\theta_2} = m_2\lambda$$

$$n_f = \{(m_1^2 \sin^2\theta_2 - m_2^2 \sin^2\theta_1)/(m_1^2 - m_2^2)\}^{\frac{1}{2}}$$

wherein $m_1$ and $m_2$ represent said orders of interference, $n_f$ represents said refractive index of said thin film, and d represents said thickness of said thin film, to calculate refractive indices $n'_f$ of said thin film on the basis of said wavelength $\lambda'$, said determined incident angle $\theta_3$ and said calculated thickness d as varying an order of interference m as a parameter according to the following equation:

$$n'_f = \{(m^2 \cdot \lambda'^2 / 4d^2) + \sin^2\theta_3\}^{\frac{1}{2}}$$

to compare a value of each of said calculated refractive indices $n_f$ with another value of each of said calculated refractive indices $n'_f$ with respect to a pair of said calculated refractive indices $n_f$ and $n'_f$ which represent an identical thickness, to determine a pair of refractive indices $n_f$ and $n'_f$ as genuine refractive indices for said wavelengths $\lambda$ and $\lambda'$, and to specify a film thickness corresponding to said specified refractive indices $n_f$ and $n'_f$ as a genuine value of said thickness of said thin film.

2. An apparatus for measuring a refractive index and a thickness of a thin film according to claim 1, wherein said first light source comprises a first laser source emitting a first laser beam, and said second light source comprises a second laser beam having a wavelength different from a wavelength of said first laser beam.

3. An apparatus for measuring a refractive index and a thickness of a thin film according to claim 1, wherein said light changing means comprises a shutter disposed on optical paths of each of said emitted first monochromatic light and said emitted second monochromatic light.

4. An apparatus for measuring a refractive index and a thickness of a thin film according to claim 1, wherein said incident angle changing means comprises a rotational turn table on which said substrate is mounted.

5. An apparatus for measuring a refractive index and a thickness of a thin film according to claim 4, wherein said incident angle changing means comprises a sensor disposed on an arm which is adapted so as to be coaxial with said turn table and adapted so that a rotation angle of said arm is always twice as large as that of said turn table.

6. An apparatus for measuring a refractive index and a thickness of a thin film according to claim 1, wherein said light changing means comprises an optical system adapted so that said selected monochromatic light is first expanded in a diameter of a beam thereof and then said expanded monochromatic light is converged on said substrate by a condenser lens in such a manner that monochromatic lights having wavelengths different from one another are simultaneously irradiated on said thin film.

7. An apparatus for measuring a refractive index and a thickness of a thin film according to claim 6, wherein said detection means comprises a photosensor array capable of detecting simultaneously reflection lights reflected from said substrate at different reflection angles.

8. An apparatus for measuring a refractive index and a thickness of a thin film according to any one of claim 1 to 7, further comprising a polarization means for changing said selected monochromatic light to an s-polarized light.

* * * * *

UNITED STATES PATENT AND TRADEMARK OFFICE
CERTIFICATE OF CORRECTION

PATENT NO. : 5,034,617
DATED : 07/23/91
INVENTOR(S) : TAMI ISOBE

It is certified that error appears in the above-identified patent and that said Letters Patent is hereby corrected as shown below:

Column 3, line 1, change "$n_f = \{(m_1^2 \cdot SIN^2\theta_2 - m_2^2 \cdot SIN^2\theta_1)/(m_1^2 - m_2^2)\}^{\frac{1}{2}}$"

to --$n_f = \{(m_1^2 \sin^2\theta_2 - m_2^2 \sin^2\theta_1)/(m_1^2 - m_2^2)\}^{\frac{1}{2}}$--.

Column 4, line 5, change "$n_f = \{(m^2 \cdot \lambda^2/4d^2) + SIN^2\theta\}^{\frac{1}{2}}$" to --$n'_f = \{(m^2 \cdot \lambda'^2/4d^2) + \sin^2\theta_3\}^{\frac{1}{2}}$--.

Column 9, line 64, change "$n_f = \{(m_1^2 \sin^2\theta_2 - m_2^2 \sin^2\theta_1)/(m_1^2 - m_2^2)\}^{\frac{1}{2}}$"

to --$n_f = \{(m_1^2 \sin^2\theta_2 - m_2^2 \sin^2\theta_1)/(m_1^2 - m_2^2)\}^{\frac{1}{2}}$--.

UNITED STATES PATENT AND TRADEMARK OFFICE
CERTIFICATE OF CORRECTION

PATENT NO. : 5,034,617

DATED : 07/23/91

INVENTOR(S) : TAMI ISOBE

It is certified that error appears in the above-identified patent and that said Letters Patent is hereby corrected as shown below:

Column 10, line 10, change "$n'_f = \{(m^2 \cdot \lambda'^2/4d^2) + \sin^2\theta_3\}^{\frac{1}{2}}$" to --$n'_f = \{(m^2 \cdot \lambda'^2/4d^2) + \sin^2\theta_3\}^{\frac{1}{2}}$--.

Signed and Sealed this

Twenty-seventh Day of April, 1993

*Attest:*

MICHAEL K. KIRK

*Attesting Officer*     *Acting Commissioner of Patents and Trademarks*